(12) United States Patent
Subramanian et al.

(10) Patent No.: US 11,246,539 B2
(45) Date of Patent: Feb. 15, 2022

(54) AUTOMATED DETECTION AND TYPE CLASSIFICATION OF CENTRAL VENOUS CATHETERS

(71) Applicant: INTERNATIONAL BUSINESS MACHINES CORPORATION, Armonk, NY (US)

(72) Inventors: Vaishnavi Subramanian, Champaign, IL (US); Hongzhi Wang, San Jose, CA (US); Tanveer Syeda-Mahmood, Cupertino, CA (US); Joy Tzung-yu Wu, San Jose, CA (US); Chun Lok Wong, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 243 days.

(21) Appl. No.: 16/599,824

(22) Filed: Oct. 11, 2019

(65) Prior Publication Data
US 2021/0106286 A1    Apr. 15, 2021

(51) Int. Cl.
*A61B 5/00*    (2006.01)
*G06T 7/10*    (2017.01)
(Continued)

(52) U.S. Cl.
CPC ............ *A61B 5/7267* (2013.01); *G06K 9/685* (2013.01); *G06N 3/08* (2013.01); *G06T 7/10* (2017.01);
(Continued)

(58) Field of Classification Search
CPC ..... A61B 5/7267; A61B 2576/00; G06T 7/10; G06T 2207/20084; G06T 2207/30021;
(Continued)

(56) References Cited

U.S. PATENT DOCUMENTS

| 2010/0098314 A1 | 4/2010 | Huo et al. |
| 2013/0322725 A1* | 12/2013 | Enzmann ............... G06T 7/0012 382/132 |
| 2019/0139259 A1* | 5/2019 | Zhang ................... A61B 90/37 |

FOREIGN PATENT DOCUMENTS

WO    2018094033 A1    5/2018

OTHER PUBLICATIONS

Location identification of catheters, Keller et al, 2007; https://www.spiedigitallibrary.org/conference-proceedings-of-spie/6514/651410/Semi-automated-location-identification-of-catheters-in-digital-chest-radiographs/10.1117/12.707769.full (Year: 2007).*

(Continued)

*Primary Examiner* — Jianxun Yang
(74) *Attorney, Agent, or Firm* — Michael Best & Friedrich LLP (57) ABSTRACT

A system for automated detection and type classification of central venous catheters. The system includes an electronic processor that is configured to, based on an image, generate a segmentation of a potential central venous catheter using a segmentation method and extract, from the segmentation, one or more image features associated with the potential central venous catheter. The electronic processor is also configured to, based on the one or more image features, determine, using a first classifier, whether the image includes a central venous catheters and determine, using a second classifier, a type of central venous catheter included in the image.

14 Claims, 4 Drawing Sheets
(3 of 4 Drawing Sheet(s) Filed in Color)

(51) Int. Cl.
  *G06K 9/68* (2006.01)
  *G06N 3/08* (2006.01)
(52) U.S. Cl.
  CPC ............... *G06K 2009/6864* (2013.01); *G06T 2207/20084* (2013.01); *G06T 2207/30021* (2013.01)
(58) Field of Classification Search
  CPC ......... G06T 7/0012; G06T 2207/10116; G06T 2207/30061; G06K 9/685; G06K 2009/6864; G06N 3/08
  See application file for complete search history.

(56) References Cited

OTHER PUBLICATIONS

Random Forests approach, Yao et al, 2013; https://reader.elsevier.com/reader/sd/pii/S0022030213005432?token=52382BD45F7BF7153C2FA1BC9572AF65D7CFDEA29D76CC149AAC9A4F5A1596DEC37D9BBBC3A10F77C2FECF7E65B2E02D&originRegion=us-east-1&originCreation=20210808063421 (Year: 2013).*

Superior Vena Cava, Sonavane et al, 2015; https://pubs.rsna.org/doi/pdf/10.1148/rg.2015150056 (Year: 2015).*

X. Yi et al., "Automatic catheter detection in pediatric X-ray images using a scale-recurrent network and synthetic data." (Submitted on Jun. 4, 2018), https://arxiv.org/abs/1806.00921.

C. Mercan and M. Celebi, "An approach for chest tube detection in chest radiographs." IET Image Process., 2014, vol. 8, iss. 2, pp. 122-129.

B. Ramakrishna et al., "An improved automatic computer aided tube detection and labeling system on chest radiographs", Proc. SPIE 8315, Medical Imaging 2012: Computer-Aided Diagnosis, 83150R (Feb. 23, 2012); https://doi.org/10.1117/12.911839.

Z. Huo et al., "Computer-aided interpretation of ICU portable chest images: automated detection of endotracheal tubes", Proc. SPIE 6915, Medical Imaging 2008: Computer-Aided Diagnosis, 69152J (Mar. 17, 2008) https://doi.org/10.1117/12.770546.

K. Bingham, "Pseudo Random Forests for Feeding Tube Identification," M.S. Thesis, Dept. Comput. Sci., Univ. Missouri, Kansas City, 2015.

P. Lakhani, "Deep Convolutional Neural Networks for Endotracheal Tube Position and X-ray Image Classification Challenges and Opportunities." J. Digit Imaging. Aug. 2017; 30(4): 460-468.

* cited by examiner

AUTOMATED DETECTION AND TYPE CLASSIFICATION OF CENTRAL VENOUS CATHETERS

SUMMARY

Central venous catheters (CVCs) are commonly used in critical care settings and surgeries to monitor a patient's heart function and deliver medications close to the heart. CVCs are inserted centrally or peripherally through the jugular, subclavian, or brachial veins and are advanced toward the heart through the venous system. Anterior-posterior (AP) chest X-Rays (CXRs) obtained after one or more CVC are inserted are often used to rule out malpositioning of a CVC or other complications associated with a CVC. Analysis of CXRs to rule out malpositionings of CVCs or other complications associated with the CVC is currently done manually by a radiologist.

Automated detection and recognition of CVCs through direct whole image based recognition approaches is unlikely to yield good results. This is due to the fact that it is difficult to learn discriminative features from thin tubular structures, such as CVCs, that typically occupy less than 1% of an image.

Accordingly to address these and other deficiencies, embodiments described herein provide methods and systems for automatically determining the presence and type of a CVC included in a chest X-ray. The automatic analysis of chest X-rays expedites clinical workflows associated with CVCs and more accurately detect problems with the positioning and insertion of a CVC by avoiding human errors. For example, when a radiologist improperly classifies an inserted CVC based on a medical image, the radiologist may apply the wrong standards for determining whether the CVC is positioned correctly as different types of CVCs may have different optimized placement for the tips.

As described below, embodiments described herein detect and distinguish between four common types of CVCs, namely, peripherally inserted central catheters (PICC), internal jugular (IJ) catheters, subclavian catheters, and Swan-Ganz catheters. Detecting the existence and type of CVC included in a CXR is performed by augmenting the detection of CVCs using shape priors (described below) based on segmentations of CVCs to focus on relevant regions for classification.

For example, one embodiment provides a system for automated detection and type classification of central venous catheters. The system includes an electronic processor that is configured to, based on an image, generate a segmentation of a potential central venous catheter using a segmentation method and extract, from the segmentation, one or more image features associated with the potential central venous catheter. The electronic processor is also configured to, based on the one or more image features, determine, using a first classifier, whether the image includes a central venous catheters and determine, using a second classifier, a type of central venous catheter included in the image.

Another embodiment provides a method for automated detection and type classification of central venous catheters. The method includes, based on an image, generating a segmentation of a potential central venous catheter using a segmentation method and extracting, from the segmentation, one or more image features associated with the potential central venous catheter. The method also includes, based on the one or more image features, determining, using a first classifier, whether the image includes a central venous catheters and determining, using a second classifier, a type of central venous catheter included in the image.

Other aspects of the embodiments will become apparent by consideration of the detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

As described above, embodiments described herein provide methods and systems for automatically detecting and type classifying of central venous catheters in CXRs. Due to the small footprint of CVCs, it is difficult for deep learning networks to detect these structures based on whole image input. Accordingly, embodiments described herein use a deep learning segmentation U-Net to determine an approximate segmentation of a CVC. Utilizing, among other things, spatial priors generated by analyzing a plurality of CXRs (for example, annotated CXRs), one or more image features are extracted from the approximate segmentation of the CVC. The extracted image features are used by one or more random forests to determine whether a CVC is included in a CXR and, if a CVC is in CXR, the type of CVC.

Figure 1:
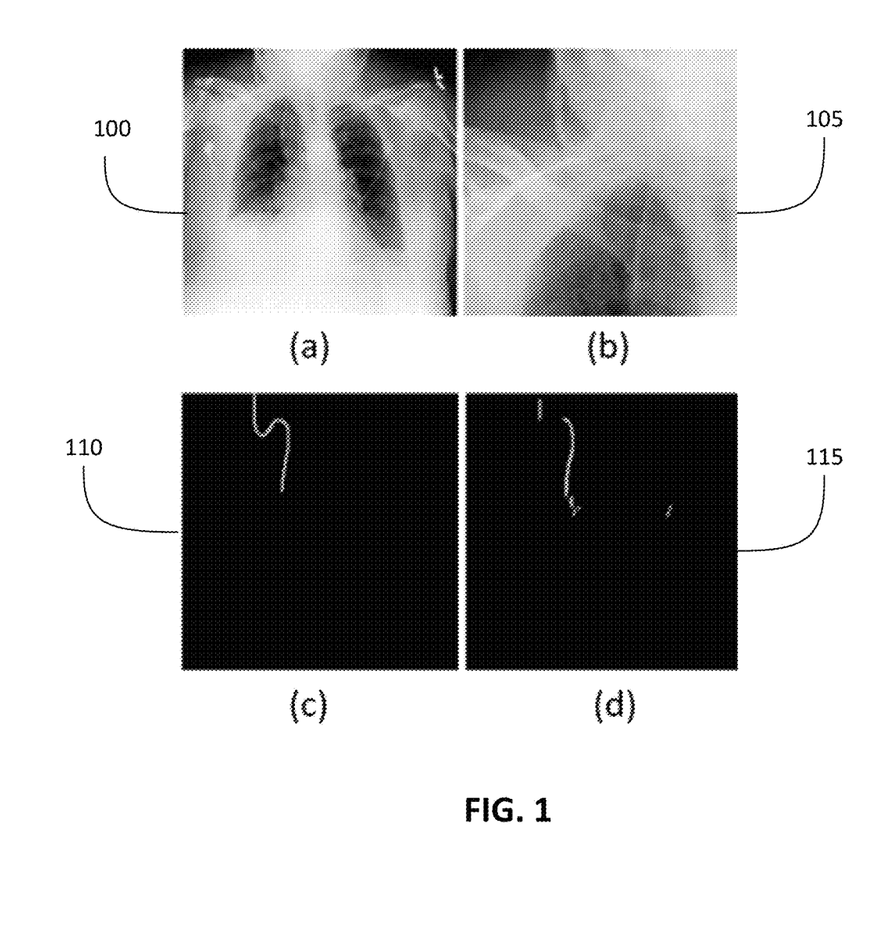
FIG. 1 illustrates an example CXR and an example segmentation of a CVC included in the CXR.

FIG. 1 illustrates an example of a CXR including a CVC. Image 100 is a CXR including a CVC, and image 105 is an enlarged version of the image 100 that has been cropped to include only the relevant region of the image 100 for the classification of the CVC included in the CXR. Image 110 is an example of a segmentation of a CVC in a CXR (specifically, the CVC included in the image 100) annotated by a radiologist. Image 115 is an example of a segmentation of a CVC in a CXR (specifically, the CVC included in the image 100) using a U-Net.

Recognizing the identity of CVCs can be a challenge since different CVCs have different contours depending on the origin of insertion and how far they extend into the body. However, despite the various CVC insertion approaches, the shape of each type of CVC has a distinctive signature and distinctive proximity patterns to known anatomical structures. Accordingly, annotated CXRs can be used to identify CVCs in images. The annotation illustrated in FIG. 1 represent traces from an anatomical origin of insertion to the tip to highlight contours that distinguish different types of CVCs from one another. However, in some embodiments, radiologist annotations may not trace the entire path of a CVC.

Figure 2:
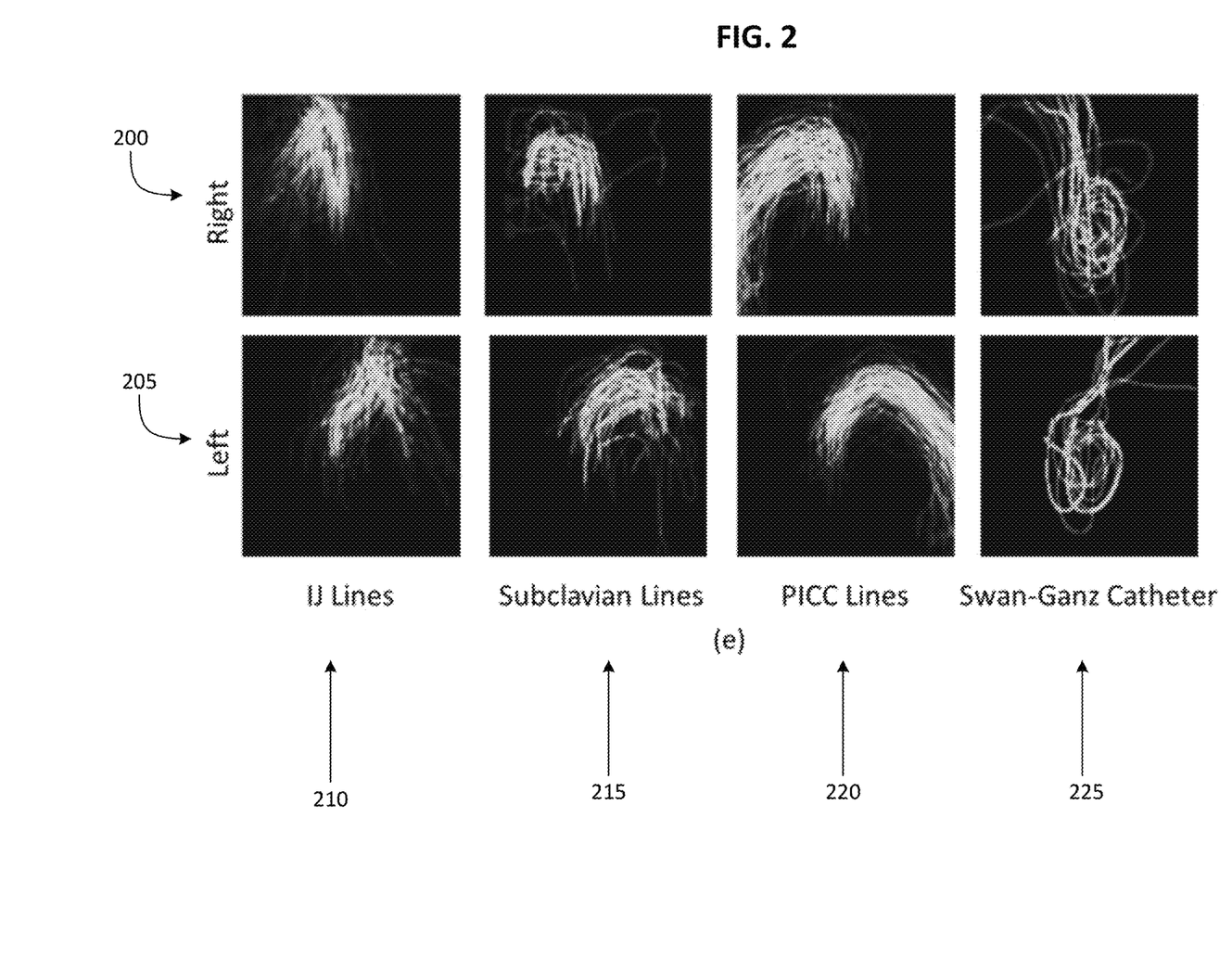
FIG. 2 illustrates spatial priors for different types of CVCs.

These annotated CXRs can be used to establish spatial priors for a type of CVC. For example, spatial priors for each type of CVC are illustrated in FIG. 2. For each type of CVC (PICC, IJ, subclavian, and Swan-Ganz), a plurality of radiologist annotated CVC segmentations, wherein the CVC is inserted through the right-hand side of a patient's body, are averaged pixel by pixel and blurred spatially to obtain a spatial prior for the type of CVC (when the CVC is inserted through the right-hand side of a patient's body. Also, for each type of CVC (PICC, IJ, subclavian, and Swan-Ganz), a plurality of radiologist annotated CVC segmentations, wherein the CVC is inserted through the left-hand side of a patient's body, are averaged pixel by pixel and blurred spatially to obtain a spatial prior for the type of CVC when the CVC is inserted through the left-hand side of a patient's body. FIG. 2 shows, for each type of CVC, two spatial priors. The top row of spatial priors 200 illustrate CVCs that are inserted through the right-hand side of a patient's body, and the bottom row of spatial priors 205 illustrate CVCs that are inserted through the left-hand side of a patient's body. Each column of spatial priors illustrates a different type of CVC. Leftmost column 210 includes spatial priors illustrating spatial signatures of IJ catheters, second from leftmost column 215 includes spatial priors illustrating spatial signatures of subclavian catheters, second from rightmost column 220 includes spatial priors illustrating spatial signatures of PICCs, rightmost column 225 includes spatial priors illustrating spatial signatures of Swan-Ganz catheters. The unique spatial signatures of the CVCs are used by the embodiments described herein to both confirm the presence of CVCs as well as determine their type.

Specifically, embodiments described herein produce a segmentation of a CVC in a CXR using a deep learning segmentation U-Net (a second U-Net as described below) trained using radiologist-produced CVC segmentations and based on U-Net, which is a convolutional neural network (CNN) architecture. Using spatial priors (based on radiologist annotated CVC segmentations) and the spatial relation of catheters to anatomical features, embodiments described herein determine the type of CVC included in a CXR using random forests. The utilization of spatial priors allows for the presence and type of CVC to be determined in a CXR without requiring that the entire CVC be detected or annotated in the CVC segmentation produced by the deep learning segmentation U-Net.

Figure 3:
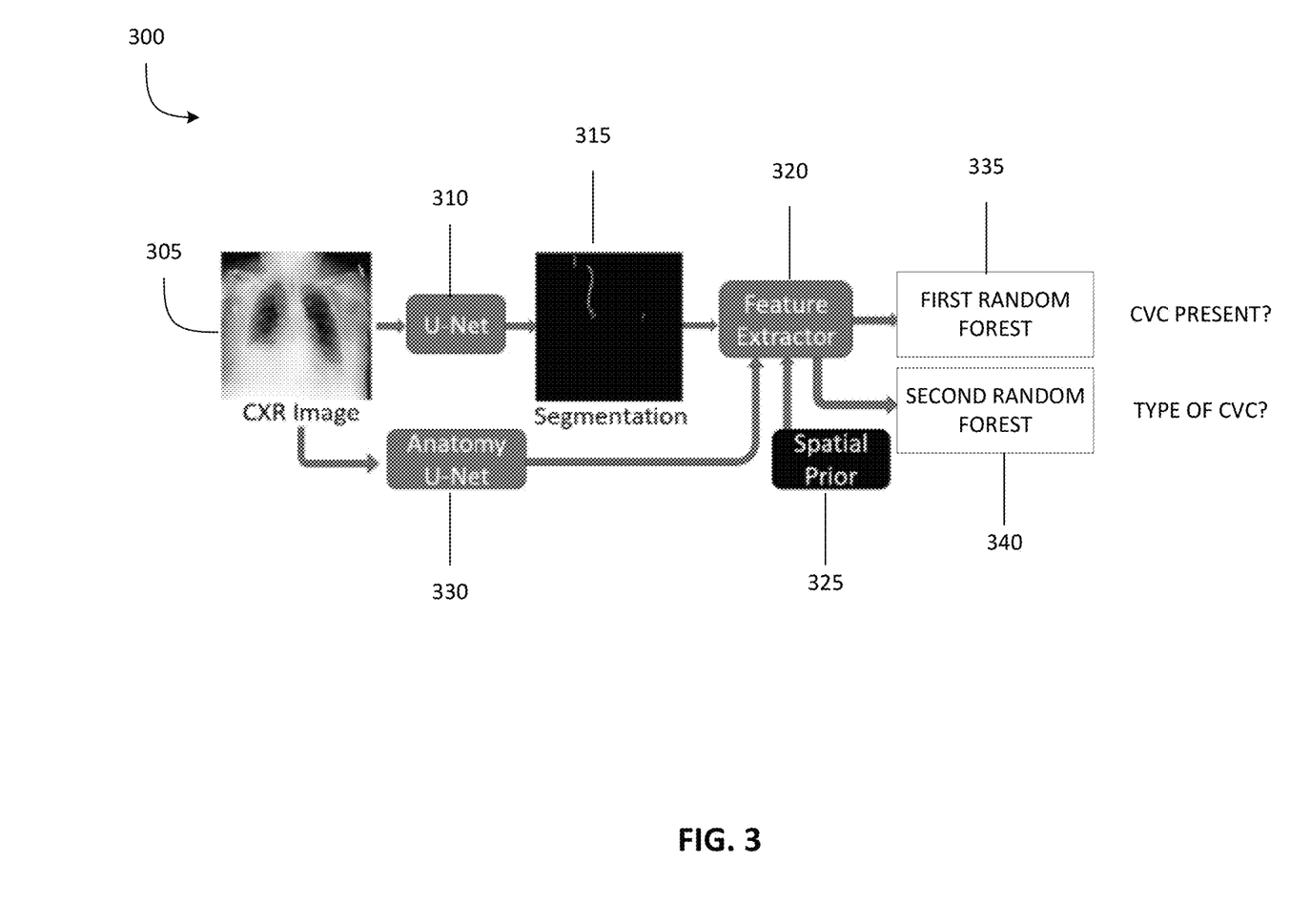
FIG. 3 illustrates an example machine learning system for automated detection and type classification of central venous catheters.

FIG. 3 provides a graphical illustration of an example method 300 for automated detection and type classification of CVCs. Image 305 is an example CXR needing analysis to detect the presence and type of an CVC. At block 310, a CXR is analyzed by a deep learning segmentation U-Net to produce a CVC segmentation (for example the CVC segmentation 315). As noted above, due to the small structure of the CVC, the loss function of the commonly utilized U-Net does not work well. Therefore, the deep learning segmentation U-Net utilized at block 310 includes a loss function developed for the segmentation of small structures (relative to image size) in place of the loss function commonly used in U-Nets. For example, the loss function may be an exponential logarithmic loss function such as the exponential logarithmic loss function described in Section 2.2 of the paper titled "3D Segmentation with Exponential Logarithmic Loss for Highly Unbalanced Object Sizes" by Ken C. L. Wong, Mehdi Moradi, Hui Tang, and Tanveer Syeda-Mahmood. It should be noted that, when a CXR does not include a CVC, the CVC segmentation output by the deep learning segmentation U-Net at block 310 is a blank image, representing no interesting region. It should also be noted that the CVC segmentation output by the deep learning segmentation U-Net at block 310 may erroneously have indicated the presence of CVC. Therefore, the CVC included in the CVC segmentation may be referred to herein as a potential CVC.

Using a CVC segmentation (for example, the CVC segmentation 315) from the deep learning segmentation U-Net at block 310, one or more image features describing the CVC segmentation are extracted from the CVC segmentation at bock 320. In some embodiments, the image features describe the CVC segmentation's relation to determined CVC contours or shapes, the segmentation's relation to anatomical features, both, or the like. The image features describe the overall properties of a potential CVC included in a CVC segmentation, even if the segmentation is imperfect. For example, the as illustrated in FIG. 1, a CVC segmentation output by the deep learning segmentation U-Net (image 115) may not be as accurate or detailed as a segmentation produced by a radiologist (image 110) and therefore imperfect.

In some embodiments, image features are extracted at block 320 using the left-hand side and right-hand side spatial priors for each type of CVC (PICC, IJ catheters, subclavian catheters, and Swan-Ganz catheters) that are obtained as described above with relation to FIG. 2. The spatial priors are represented in FIG. 3 by block 325. A pixel-wise multiplication of the segmentation output at block 310 with the each determined spatial prior (left-hand side PICC spatial prior, right-hand side PICC spatial prior, left-hand side IJ spatial prior, right-hand side IJ spatial prior, left-hand side subclavian spatial prior, right-hand side subclavian spatial prior, left-hand side Swan-Ganz spatial prior, and right-hand side Swan-Ganz spatial prior) is performed. The result of the pixel-wise multiplication is characterized using a n-bit intensity histogram of oriented gradients (HoG) to determine how well the segmentation produced at block 310 aligns with each spatial prior.

In some embodiments, the image features are extracted at block 320 using segmentations of one or more chest anatomical structures. The chest anatomical structures may be, for example, clavicles, lungs, heart and mediastinum. Segmentations for the chest anatomical structures are determined at block 330 using an anatomy U-Net (a first U-Net) that is trained using CXRs that include one or more anatomic structures annotated by a radiologist. Using the segmentations of chest anatomical structures determined by the anatomy U-Net at block 330 and the CVC segmentation determined by the U-Net at block 310, the Euclidean distance distributions of the CVC segmentation relative to the center of different chest anatomical structures are determined. The Euclidian distance distributions are image features that provide contextual information and help to distinguish, for example, PICCs from subclavian catheters.

In some embodiments, the image features extracted at block 320 include shape and size properties of a potential CVC included in a CXR. Size and shape properties of a CVC may include, for example, area, length and width of a potential CVC. While the image features extracted using spatial priors are particularly useful in determining a type of CVC included in the CXR, the size and shape properties are particularly useful in determining whether a CVC is present in a CXR.

In some embodiments, the image features are passed to one or more machine learning models for analysis to determine whether a CVC is present in a CXR and a type of CVC present in a CXR. In the example embodiment illustrated in FIG. 3, the image features extracted at block 320 are passed to a first random forest 335 (a first classifier) that is configured to determine whether a CVC is present in a CXR. For example, the first random forest 335 yields a binary presence/absence label. In some embodiments, the image features extracted at block 320 are also passed to a second random forest 340 (a second classifier) that is configured to identify a type of CVC included in the CRX. For example, the second random forest 340 may provide a multi-label output, with four indicators, one for each type of CVC (PICC, IJ, subclavian, and Swan-Ganz).

The example embodiment illustrated in FIG. 3 was created after experimenting with a plurality of different end-to-end machine learning systems. These experiments and their results are described in detail in the following paragraphs.

In the experiments, a dataset of 112,000 CXRs were used. A first subset of the CXRs of 1500 AP CXRs was selected from the dataset. The CXRs included in the first subset that showed CVCs were labeled and annotated by a radiologist at the pixel level to provide annotations of 359 IJ catheters, 78 subclavian catheters, 277 PICCs, and 32 Swan-Ganz catheters, yielding a total of 608 512 pixel×512 pixel images including annotated CVCs. The remaining 892 images had no catheters.

A second subset of 3000 CXRs was also selected from the dataset. The CXRs included in the second subset were a labeled by a radiologist to indicate whether an external medical device was shown in a CXR. Approximately 2381 CXRs were labeled as including an external medical device, and 619 CXRs were labeled as being devoid of an external medical device. Since external medical devices included in CXRs are usually catheters, CXRs that were labeled as including an external medical device were considered to include a CVC.

A third subset of around 16,000 CXRs was selected from the dataset and radiologists labeled each CXR included in the third subset for the presence of different CVCs. This resulted in 10,746 CXRs labeled as including at least one type of externally inserted catheter, with CXRs 4249 labeled as including a PICC, 1651 CXRs labeled as including an IJ catheter, 201 CXRs labeled as including a subclavian catheter, 192 CXRs labeled as including a Swan-Ganz catheter, and 4453 CXRs labeled as including a another type of catheter (for example, an airway tube or a drainage tube).

In this experiment the deep learning segmentation U-Net used in block 310 of FIG. 3 was trained to determine CVC segmentations as discussed above, treating the radiologist annotated CVCs from the dataset as belonging to a positive class without specific distinction on CVC type. For example, as part of this training, the pixel-level annotated images were split so that 80 percent of the annotated images are included in a training set and 20 percent of the annotated images are included in a validation set. The deep learning segmentation U-Net was trained until convergence was achieved using the Adam optimizer with learning rate of 5e-5 and the exponential loss with the best-performing weights ($w_{Dice}=0.8$ and $w_{Cross}=0.2$).

The quality of the CVC segmentations produced by the deep learning segmentation U-Net were evaluated by computing the extent of overlap between the ground truth annotations and CVC segmentations produced by the deep learning segmentation U-Net. Since CVCs are thin structures, for reliable overlap estimation between radiologist produced and deep learning segmentation U-Net produced CVC segmentations, the radiologist-produced segmentations were enlarged via a dilation operation. With a 2-pixel dilation radius, 75 percent of pairs of radiologist and deep learning segmentation U-Net produced segmentations have an overlap of over 50 percent and 84 percent of pairs of radiologist and deep learning segmentation U-Net produced segmentations have an overlap of over 40 percent and a 5-pixel dilation radius resulted in 80 percent and 90 percent of pairs of radiologist and deep learning segmentation U-Net produced segmentations with greater than an overlap of 50 percent and an overlap of 40 percent overlap, respectively.

To determine the presence of a CVC in a CXR a 5-fold cross-validation was performed using the second subset of CXRs and a 60-20-20 split for training-validation-testing. A number of machine learning systems were tested to determine the machine learning system that best detected the presence of a CVC in a CXR. Each machine learning system was configured to output a binary label indicating the presence of at least one CVC in a CXR (label 1), or the absence of any CVCs (label 0). Results regarding the performance of each machine learning system are presented in Table 1. In Table 1, each row represents a machine learning system. The specific machine learning system is indicated in the column labeled "Method." In Table 1, the column labeled 'P' contains the precision of each machine learning system, the column labeled 'R' contains the recall of each machine learning system, the column labeled "Acc" contains the accuracy of each machine learning system, and the column labeled "AUC" contains the area under an receiver operating characteristic (ROC) curve for each machine learning system. It should be noted that the values included in Table 1 are percentages.

TABLE 1

| Method | P | R | Acc | AUC |
|---|---|---|---|---|
| 1. DN | 20.0 | 20.0 | 20.0 | 50.0 |
| 2. VGG | 20.0 | 20.0 | 20.0 | 50.0 |
| 3. DN + VGG | 81.6 | 95.0 | 75.3 | 63.0 |
| 4. DN-RF | 79.4 | 98.8 | 78.8 | 50.2 |
| 5. VGG-RF | 79.4 | 98.0 | 78.4 | 50.0 |
| 6. Seg-DN-RF | 80.0 | 95.8 | 77.8 | 58.6 |
| 7. +CXR | 79.6 | 97.2 | 78.4 | 51.4 |
| 8. Seg-VGG-RF | 80.2 | 95.0 | 78.2 | 53.6 |
| 9. +CXR | 79.2 | 97.2 | 79.8 | 49.8 |
| 10. Mask-DN-RF | 84.0 | 92.4 | 79.4 | 62.0 |
| 11. Mask-VGG-RF | 84.2 | 91.6 | 79.6 | 62.8 |
| 12. Seg-SP-RF (Ours) | 89.6 | 89.6 | 83.8 | 75.0 |
| 13. +HoG (Ours) | 91.4 | 89.4 | 85.2 | 78.8 |
| 14. +Anatomy (Ours) | 91.6 | 89.6 | 85.2 | 79.4 |

A Visual Geometry Group (VGG)16 and a DenseNet neural network were pre-trained using ImageNet and fine-tuned using the second subset of CXRs to determine the presence of a CVC in a CXR. The VGG16 and DenseNet neural network yield poor results, with less than 50% accuracy (see rows 1-2 of Table 1). Concatenating the features from DenseNet and VGG16 and performing heavy hyper-parameter tuning resulted in a moderately improved performance (see row 3 of Table 1). Overall, the VGG16 and DenseNet neural networks were unable to recognize the discriminative regions and performed poorly, due to the small footprint of CVCs in CXRs, long tubular structures of CVCs that blend into the background of CXRs, and uneven sample sizes. Thus, in further experiments, the VGG16 and DenseNet neural networks were used as feature extractors, feeding their pre-final layer outputs to random forest classifiers. Combining the VGG16 and DenseNet neural networks with random forest classifiers resulted in improved accuracy, while the area under ROC (AUC) still remained at 50% (see rows 4-5 of Table 1).

Next, CXRs were analyzed by the U-Net described above to generate CVC segmentations. The combinations of the segmentations and the original CXR image were analyzed by the VGG16 and DenseNet neural networks. Row 6 of Table 1 illustrates the results achieved when a CVC segmentation alone is analyzed by a DenseNet neural network with a random forest classifier. Row 7 of Table 1 illustrates the results achieved when a CVC segmentation and a CXR that the CVC segmentation is based on are both analyzed by a DenseNet neural network with a random forest classifier. Row 8 of Table 1 illustrates the results achieved when a CVC segmentation alone is analyzed by a VGG16 neural network with a random forest classifier. Row 9 of Table 1 illustrates the results achieved when a CVC segmentation and a CXR that the CVC segmentation is based on are both analyzed by a VGG16 neural network with a random forest classifier. Row 10 of Table 1 illustrates the results achieved when a CXR is masked to create a masked CXR focused on regions of potential CVCs and the masked CXR is analyzed by a DenseNet neural network with a random forest classifier. Row 11 of Table 1 illustrates the results achieved when a CXR is masked to create a masked CXR focused on regions of potential CVCs and the masked CXR is analyzed by a VGG16 neural network with a random forest classifier. The systems in rows 6-11 of Table 1 showed considerable improvements in the AUC compared to the systems in rows 1-5 of Table 1, while the other metrics (precision, recall, F-score and accuracy) remained primarily unchanged.

Finally, image-processing features describing the size, shape, likelihood based on CVC spatial priors, and relation to chest anatomical elements, as were determined from a CRX image as described above. As can be seen in row 12 of Table 1, analyzing, with a random forest classifier, a set of features comprising spatial prior information and a CVC segmentation determined by a U-Net as described above yielded a 12% increase in AUC. Row 13 illustrates the improvements in performance when size and HoG shape features were added to the set of features analyzed by the random forest classifier. Row 14 illustrates the improvements in performance when anatomical relation information were added to the set of features analyzed by the random forest classifier. The machine learning system in row 14 has 85.2% accuracy at a precision of 91.6% and a recall of 89.6%.

To identify the type of CVC present, a 5-fold cross-validation was performed with the 10,746 labeled CXRs of the third subset of CXRs using a 60-20-20 split for training-validation-testing. A number of machine learning systems were tested to determine the machine learning system that best determine a type of CVC included in a CXR. Like in Table 1, in Table 2, each row represents a machine learning system. The specific machine learning system is indicated in the column labeled "Method." For each type of CVC (PICC, IJ, Subclavian, Swan-Ganz), Table 2 includes a column labeled 'P' that contains the precision of each machine learning system and a column labeled 'R' that contains the recall of each machine learning system. Table 2 also includes, for each machine learning system, a weighted average of the precision, recall, accuracy (included in the column labeled "Accuracy"), area under a receiver operating characteristic (ROC) curve (the column labeled "AUC") of each type of CVC. It should be noted that the values included in Table 1 are percentages and the values following the ±symbol represent the standard deviation. The best or highest values in each column are bolded. Every machine learning system included in Table 1 is also included in Table 2 except the machine learning system that is a concatenation of a DenseNet neural network and a VGG16 neural network.

As illustrated in Table 2, the best performing machine learning system (included in row 13) was that which has been described above (specifically, with relation to FIG. 3). The recall of the best performing machine learning system for CVCs other than PICCs is under 50%. This is primarily due to the fact that PICC CVCs (while having the simplest contours) make up about 40% of the CXRs of the third subset of CXRs labeled as including CVCs. More complex contours like the Swan-Ganz are under-represented and comprise only 2% of the CXRs of the third subset of CXRs labeled as including CVCs. The recall of the best performing machine learning system for CVCs other than PICCs could be improved by obtaining more training data for these types of CVCs.

TABLE 2

| | PICC | | IJ | | SC | | SG | | Weighted Average | | | |
|---|---|---|---|---|---|---|---|---|---|---|---|---|
| Method | P | R | P | R | P | R | P | R | P | R | Accuracy | AUC |
| 1. DN | 34.6 | 11.6 | 13.2 | 22.2 | 0.0 | 0.0 | 2.6 | 51.4 | 34.2 | 20.4 | 20.0 ± 0.71 | 51.0 ± 1.00 |
| 2. VGG | 36.6 | 2.8 | 16.6 | 8.8 | 1.2 | 16.8 | 2.8 | 6.2 | 36.0 | 27.6 | 28.0 ± 0.00 | 48.6 ± 0.89 |
| 3. DN-RF | 78.4 | 55.0 | 96.6 | 32.4 | 100.0 | 33.8 | 100.0 | 25.8 | 84.6 | 47.4 | 66.2 ± 1.10 | 67.0 ± 0.71 |
| 4. VGG-RF | 77.2 | 54.6 | 96.4 | 32.2 | 100.0 | 33.2 | 100.0 | 25.8 | 83.8 | 47.2 | 65.6 ± 0.89 | 66.8 ± 0.84 |
| 5. Seg-DN-RF | 77.4 | 64.8 | 84.2 | 38.2 | 100.0 | 33.2 | 100.0 | 24.6 | 80.8 | 55.4 | 68.6 ± 0.89 | 68.6 ± 0.89 |
| 6. +CXR | 78.2 | 52.2 | 98.2 | 33.2 | 100.0 | 33.8 | 100.0 | 25.2 | 85.0 | 45.8 | 65.4 ± 1.14 | 66.8 ± 0.45 |
| 7. Seg-VGG-RF | 76.4 | 63.8 | 82.4 | 37.6 | 100.0 | 32.6 | 100.0 | 25.8 | 79.2 | 54.8 | 67.4 ± 0.55 | 68.2 ± 0.84 |
| 8. +CXR | 76.2 | 52.6 | 96.2 | 32.8 | 100.0 | 33.2 | 100.0 | 23.8 | 83.2 | 45.8 | 64.8 ± 1.30 | 66.6 ± 0.55 |
| 9. Mask-DN-RF | 75.6 | 60.0 | 88.6 | 35.6 | 100.0 | 33.8 | 100.0 | 25.2 | 80.6 | 51.6 | 66.6 ± 0.89 | 67.8 ± 0.45 |
| 10. Mask-VGG-RF | 74.6 | 58.0 | 87.2 | 34.8 | 100.0 | 33.8 | 100.0 | 25.2 | 79.2 | 50.2 | 65.4 ± 1.14 | 67.2 ± 0.84 |
| 11. Seg-SP-RF | 88.6 | 75.4 | 95.8 | 33.4 | 100.0 | 31.6 | 100.0 | 25.8 | 91.2 | 61.6 | 75.6 ± 0.55 | 70.0 ± 0.71 |
| 12. +HoG | 93.0 | 78.8 | 99.0 | 32.4 | 100.0 | 33.2 | 100.0 | 25.8 | 95.2 | 63.8 | 78.2 ± 0.84 | 70.8 ± 0.84 |
| 13. +Anatomy | 93.0 | 78.8 | 99.6 | 32.2 | 100.0 | 33.8 | 100.0 | 25.8 | 95.6 | 63.6 | 78.4 ± 0.55 | 71.0 ± 0.71 |

Figure 4:
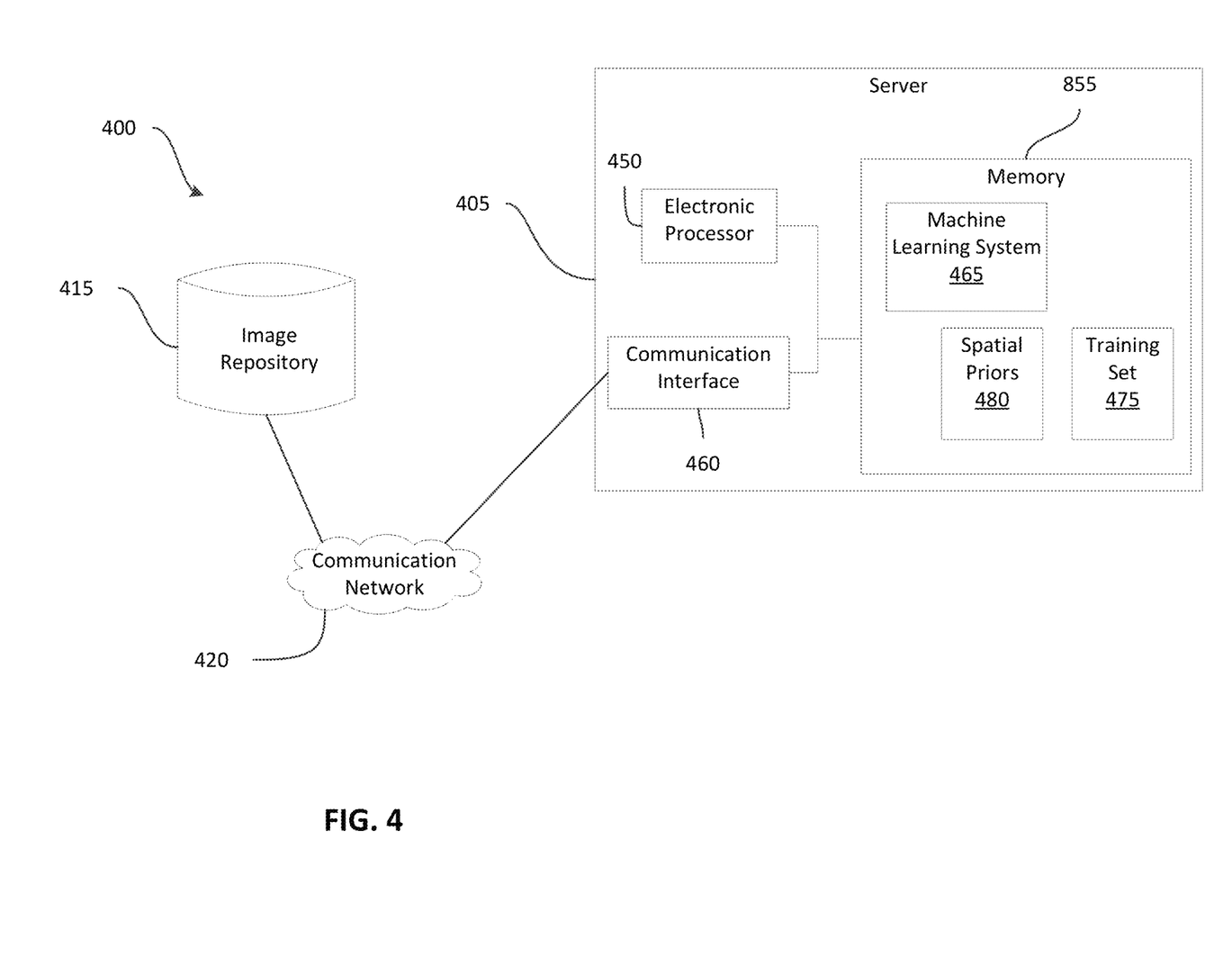
FIG. 4 schematically illustrates a system for implementing the machine learning system for automated detection and type classification of central venous catheters of FIG. 3 according to some embodiments.

It should be understood that the functionality described herein can be performed via one or more computing devices, such as one or more servers. For example, FIG. 4 illustrates a system 400 for automated detection and type classification of central venous catheters according to some embodiments. As illustrated in FIG. 4, the system 400 includes a server 405 and an image repository 415. The server 405 and the image repository 415 communicate over one or more wired or wireless communication networks 420. Portions of the wireless communication networks 420 may be implemented using a wide area network, such as the Internet, a local area network, such as a Bluetooth™ network or Wi-Fi, and combinations or derivatives thereof. It should be understood that the system 400 may include more or fewer servers and the single server 405 illustrated in FIG. 4 is purely for illustrative purposes. For example, in some embodiments, the functionality described herein is performed via a plurality of servers in a distributed or cloud-computing environment. Also, in some embodiments, the server 405 may communicate with multiple image repositories. Also, in some embodiments, the components illustrated in the system 400 may communicate through one or more intermediary devices (not shown).

In some embodiments, the image repository 415 is, for example, a picture archiving and communication system (PACS), a cloud storage environment, or the like. The images in the image repository 415 are generated by an imaging modality (not shown), such as an X-ray. In some embodiments, the image repository 415 may also be included as part of an imaging modality. The image repository 415 may include the dataset of 112,000 CXRs described above.

As illustrated in FIG. 4, the server 405 includes an electronic processor 450, a memory 455, and a communication interface 460. The electronic processor 450, the memory 455, and the communication interface 460 communicate wirelessly, over wired communication channels or buses, or a combination thereof. The server 405 may include additional components than those illustrated in FIG. 4 in various configurations. For example, in some embodiments, the server 405 includes multiple electronic processors, multiple memory modules, multiple communication interfaces, or a combination thereof. Also, it should be understood that the functionality described herein as being performed by the server 405 may be performed in a distributed nature by a plurality of computers located in various geographic locations. For example, the functionality described herein as being performed by the server 405 may be performed by a plurality of computers included in a cloud computing environment.

The electronic processor 450 may be a microprocessor, an application-specific integrated circuit (ASIC), and the like. The electronic processor 450 is generally configured to execute software instructions to perform a set of functions, including the functions described herein. The memory 455 includes a non-transitory computer-readable medium and stores data, including instructions executable by the electronic processor 450. The communication interface 460 may be, for example, a wired or wireless transceiver or port, for communicating over the communication network 420 and, optionally, one or more additional communication networks or connections.

As illustrated in FIG. 4, the memory 455 of the server 405 includes a machine learning system 465, training data 475, and spatial priors 480. It should be understood that, in some embodiments, the functionality described herein as being provided by the machine learning system 465 (or the training thereof) may be distributed and combined in various configurations, such as through multiple separate software applications. The spatial priors 480 may be determined from one or more CXRs that are received from the image repository 415 and annotated to highlight a CVCs included in them. The machine learning system 465 includes a deep learning segmentation U-Net, an anatomy U-Net, a first random forest, and a second random forest all of which are described above. In some embodiments, the training data 475 is includes multiple training sets, each of which is used to train a different component of the machine learning system 465. For example, the training data 475 may include training sets for training the deep learning segmentation U-Net, anatomy U-Net, first random forest, and second random forest. For example, a training set used to train the deep learning segmentation U-Net may include pairs of CXRs wherein one CXR is unannotated and one CXR includes an annotated CVC. A training set used to train the anatomy U-Net may include pairs of CXRs wherein one CXR is unannotated and one CXR includes one or more annotated anatomical features. A training set used to train the first random forest may include pairs of CXRs wherein one CXR is unlabeled and one CXR is labeled with a binary label indicating whether or not the CXR includes a CVC. A training set used to train the second random forest may include pairs of CXRs wherein one CXR is unlabeled and one CXR is labeled based on the type of CVC the CXR includes (PICC, IJ, subclavian, Swan-Ganz, or other). After the machine learning system 465 is trained via the training data 475, the machine learning system 465 can be used to detect and classify central venous catheters by type.

It should be understood that the machine learning system 465 may be trained to detect a different number of types of CVCs than four and that the machine learning system 465 may be trained to detect different types of CVCs than those described herein. It should also be understood that, in some embodiments, a type of image other than an AP CXR may be analyzed by the machine learning system 465 to determine whether a CVC is present and the type of CVC that is present.

It should also be understand that the embodiments described herein may be used to detect and classify other types of tubular structures in images and are not limited to detecting and classifying CVCs as provided herein as one example. Furthermore, the embodiments described herein may be used with other types of images and are not limited to chest x-rays but may be used with other types of medical images (of various anatomical regions) or even images outside of the medical industry that include tubular structures, such as thin structures that are difficult to detect and classify using whole image analysis. Additionally, other types of segmentation methods or classifiers may be used in place of the U-Nets and random forests described herein. In one example, a segmentation method such as thresholding, clustering, region growing, edge detection, partial differential equation-based methods, a combination of the foregoing, or the like may be used in place of one or both of the U-Nets included in the system 400 and method 300 described above. In another example, a neural network such as a convolutional neural network, a recurrent neural network, a combination of the foregoing, or the like may be used in place of one or both of the U-Nets included in the system 400 and method 300 described above. In yet another example, a classifier such as a linear classifier, support vector machine, decision tree, neural network, a combination of the foregoing, or the like may be used in place of the first random forest, second random forest, or both included in the system 400 and method 300 described above.

Various features and advantages of some embodiments are set forth in the following claims.

What is claimed is:

1. A system for automated detection and type classification of central venous catheters, the system comprising:
an electronic processor, the electronic processor configured to
based on an image, generate a segmentation of a potential central venous catheter using a segmentation method, wherein the image is a chest X-ray;
extract, from the segmentation, one or more image features associated with the potential central venous catheter, wherein the one or more image features are extracted using spatial prior, wherein a spatial prior is generated from a plurality of chest X-rays including central venous catheters annotated by radiologists, wherein two spatial priors, one for central venous catheters inserted through a left-hand side of a patient's body and one for central venous catheters inserted through a right-hand side of a patient's body, are generated for each type of central venous catheter;
based on the one or more image features, determine, using a first classifier, whether the image includes a central venous catheters; and
based on the one or more image features, determine, using a second classifier, a type of central venous catheter included in the image.

2. The system according to claim 1, wherein the electronic processor is configured to extract image features by performing a pixel-wise multiplication of the segmentation with the each determined spatial prior.

3. The system according to claim 1, wherein the electronic processor is further configured to determine, using a first U-Net, one or more chest anatomical structures in the image.

4. The system according to claim 3, wherein the one or more image features are extracted using Euclidean distance distributions of the segmentation relative to a center of one or more chest anatomical structures.

5. The system according to claim 1, wherein types of central venous catheters include peripherally inserted central catheters, internal jugular catheters, subclavian catheters, and Swan-Ganz catheters.

6. The system according to claim 1, wherein the segmentation method is a second U-Net and the first and second classifiers are random forests.

7. The system according to claim 6, wherein the second U-Net is trained using a plurality of chest X-rays, one or more of which include a central venous catheter annotated by a radiologist.

8. A method for automated detection and type classification of central venous catheters, the method comprising:
based on an image, generating a segmentation of a potential central venous catheter using a segmentation method, wherein the image is a chest X-ray;
extracting, from the segmentation, one or more image features associated with the potential central venous catheter wherein the one or more image features are extracted using spatial priors, and wherein a spatial prior is generated from a plurality of chest X-rays including central venous catheters annotated by radiologists, wherein two spatial priors, one for central venous catheters inserted through a left-hand side of a patient's body and one for central venous catheters inserted through a right-hand side of a patient's body, are generated for each type of central venous catheter;
based on the one or more image features, determining, using a first classifier, whether the image includes a central venous catheters; and
based on the one or more image features, determining, using a second classifier, a type of central venous catheter included in the image.

9. The method according to claim 8, wherein extracting, from the segmentation, one or more image features associated with the potential central venous catheter includes performing a pixel-wise multiplication of the segmentation with the each determined spatial prior.

10. The method according to claim 8, the method further comprising determining, using a first U-Net, one or more chest anatomical structures in the image.

11. The method according to claim 10, wherein the one or more image features are extracted using Euclidean distance distributions of the segmentation relative to a center of one or more chest anatomical structures.

12. The method according to claim 8, wherein types of central venous catheters include peripherally inserted central catheters, internal jugular catheters, subclavian catheters, and Swan-Ganz catheters.

13. The method according to claim 8, wherein the segmentation method is a second U-Net and the first and second classifiers are random forests.

14. The method according to claim 13, wherein the second U-Net is trained using a plurality of chest X-rays, one or more of which include a central venous catheter annotated by a radiologist.

* * * * *